United States Patent
Thomas et al.

(10) Patent No.: US 12,349,706 B2
(45) Date of Patent: Jul. 8, 2025

(54) COMPOSITIONS AND METHODS RELATED TO EXCIPIENTS AND CANNABINOID FORMULATIONS

(71) Applicant: Natural Extraction Systems, LLC, Boulder, CO (US)

(72) Inventors: C. Russell Thomas, Boulder, CO (US); Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 586 days.

(21) Appl. No.: 17/392,247

(22) Filed: Aug. 2, 2021

(65) Prior Publication Data

US 2021/0360947 A1 Nov. 25, 2021

Related U.S. Application Data

(60) Provisional application No. 63/228,594, filed on Aug. 2, 2021, provisional application No. 63/228,572, filed on Aug. 2, 2021, provisional application No. 63/228,563, filed on Aug. 2, 2021, provisional application No. 63/194,810, filed on May 28, 2021, provisional application No. 63/191,844, filed on May 21, 2021, provisional application No. 63/191,872, filed on May 21, 2021, provisional application No. 63/191,814, filed on May 21, 2021, provisional application No. 63/191,830, filed on May 21, 2021, provisional application No. 63/154,480, filed on Feb. 26, 2021, provisional application No. 63/154,538, filed on Feb. 26, 2021, provisional application No. 63/154,579, filed on Feb. 26, 2021, provisional application No. 63/154,507, filed on Feb. 26, 2021, provisional application No. 63/148,047, filed on Feb. 10, 2021, provisional application No. 63/130,560, filed on Dec. 24, 2020, provisional application No. 63/059,829, filed on Jul. 31, 2020.

(51) Int. Cl.
| | |
|---|---|
| A23L 2/38 | (2021.01) |
| A23L 2/395 | (2006.01) |
| A61K 9/00 | (2006.01) |
| A61K 31/00 | (2006.01) |

(52) U.S. Cl.
CPC ............ *A23L 2/38* (2013.01); *A23L 2/395* (2013.01); *A61K 9/0095* (2013.01); *A61K 31/658* (2023.05)

(58) Field of Classification Search
CPC .......... A61K 31/658; A23L 2/38; A23L 2/395
See application file for complete search history.

(56) References Cited

U.S. PATENT DOCUMENTS

| | | |
|---|---|---|
| 6,747,058 B1 | 6/2004 | Dedhiya et al. |
| 8,962,696 B2 | 2/2015 | Harris et al. |
| 9,907,823 B1 | 3/2018 | Kuhrts |
| 10,239,848 B2 | 3/2019 | Gallily et al. |
| 10,555,914 B1 | 2/2020 | Metcalf |
| 10,609,944 B1 | 4/2020 | Metcalf |
| 10,959,961 B2 | 3/2021 | Metcalf |
| 2007/0105086 A1 | 5/2007 | Qin |
| 2008/0112895 A1 | 5/2008 | Kottayil |
| 2009/0044700 A1 | 2/2009 | Dietlin |
| 2014/0023614 A1 | 1/2014 | Barawkar et al. |
| 2014/0263467 A1 | 9/2014 | Wardle |
| 2015/0320720 A1 | 11/2015 | McAllister et al. |
| 2016/0018424 A1 | 1/2016 | Lucas et al. |
| 2017/0246897 A1 | 8/2017 | Brehm et al. |
| 2018/0049994 A1 | 2/2018 | Aung-Ding |
| 2018/0169035 A1 | 6/2018 | Eyal |
| 2018/0353463 A1 | 12/2018 | Winnicki |
| 2019/0030170 A1 | 1/2019 | Kingsley et al. |
| 2020/0245666 A1* | 8/2020 | Spall ..................... A23L 2/52 |

FOREIGN PATENT DOCUMENTS

| | | |
|---|---|---|
| CA | 2760460 A1 | 11/2010 |
| CN | 108314608 A | 7/2018 |
| EP | 1361864 B1 | 12/2013 |
| EP | 3061450 A1 | 8/2016 |
| EP | 3351242 A1 | 7/2018 |
| EP | 3459536 A1 | 3/2019 |
| TW | 201718493 A | 6/2017 |
| WO | 2006130679 A2 | 12/2006 |
| WO | 2006133941 A2 | 12/2006 |
| WO | 2011104667 A1 | 9/2011 |
| WO | 2013045115 A1 | 4/2013 |
| WO | 2015052568 A2 | 4/2015 |
| WO | 2017202424 A1 | 11/2017 |
| WO | 2018158150 A1 | 7/2018 |
| WO | 2018150182 A1 | 8/2018 |
| WO | 2018183115 A1 | 10/2018 |
| WO | 2019036243 A1 | 2/2019 |
| WO | 2020123809 A1 | 6/2020 |

(Continued)

OTHER PUBLICATIONS

Alejseev et al., "Technology of raising the availability of biologic and pharmaceutical drugs," 2012, XIX(4):43-47.
Dow Corning, "Corning® Plastic Storage Bottles Selection Guide," 2016, 8 pages.
Gelderblom et al., "Cremophor EL: the drawbacks and advantages of vehicle selection for drug formulation," European Journal of Cancer, 2001, pp. 1590-1998, vol. 37.
Kogan et al., "Synthesis and antitumor activity of quinonoid derivatives of cannabinoids," Journal of Medicinal Chemistry, 2004, pp. 3800-3806, vol. 47, issue 15.
Layton et al., "Forced degradation of cannabidiol," 2016, publisher Waters Corporation, 6 pages.

(Continued)

*Primary Examiner* — Amanda L. Aguirre
*Assistant Examiner* — Chris E Simmons
(74) *Attorney, Agent, or Firm* — Douglas G. Metcalf

(57) ABSTRACT

Various aspects of this patent document relate to beverage concentrates that comprise active ingredients, containers comprising beverage concentrates, and methods to prepare beverage formulations from beverage concentrates.

18 Claims, No Drawings

(56) References Cited

FOREIGN PATENT DOCUMENTS

| WO | 2020123976 A1 | 6/2020 |
|---|---|---|
| WO | 2020264199 A1 | 12/2020 |
| WO | 2021214762 A1 | 10/2021 |

OTHER PUBLICATIONS

Martijn, "CBD products according to sensi seeds," 2016, 12 pages.
Mazina et al., "A rapid capillary electrophoresis method with LED-induced native fluorescence detection for the analysis of cannabinoids in oral fluid," Analytical Methods, 2015, pp. 7741-7747, vol. 7.
Mechoulam et al., "Hashish-X111: On the nature of the beam test," Tetrahedron, 1968, pp. 5615-5624, vol. 24, issue 16.
Mechoulam et al., "Cannabidiol: an overview of some chemical and pharmacological aspects. Part I: chemical aspects," Chemistry and Physics of Lipids, 2002, pp. 35-43, vol. 121.
Srebnik et al., "Base-catalysed double-bond isomerizations of cannabinoids: structural and stereochemical aspects," Journal of the Chemical Society, Perkin Transactions I, 1984, pp. 2881-2886.
Starks, "Marijuana Chemistry: Genetics, Processing & Potency", 2nd ed., 1990, onin Publishing, Inc. (Berkeley CA).
Wilson et al., "HU-331 and oxidized cannabidiol acts as inhibitors of human topoisomerase ll$\alpha$ and $\beta$," Chemical Research in Toxicology, 2017, pp. 137-144, vol. 31.

* cited by examiner

COMPOSITIONS AND METHODS RELATED TO EXCIPIENTS AND CANNABINOID FORMULATIONS

CROSS-REFERENCE TO RELATED APPLICATIONS

This patent application claims priority to U.S. Provisional Patent Application No. 63/059,829, filed Jul. 31, 2020; U.S. Provisional Patent Application No. 63/130,560, filed Dec. 24, 2020; U.S. Provisional Patent Application No. 63/148,047, filed Feb. 10, 2021; U.S. Provisional Patent Application No. 63/154,480, filed Feb. 26, 2021; U.S. Provisional Patent Application No. 63/154,507, filed Feb. 26, 2021; U.S. Provisional Patent Application No. 63/154,538, filed Feb. 26, 2021; U.S. Provisional Patent Application No. 63/154,579, filed Feb. 26, 2021; U.S. Provisional Patent Application No. 63/191,814, filed May 21, 2021; U.S. Provisional Patent Application No. 63/191,830, filed May 21, 2021; U.S. Provisional Patent Application No. 63/191,844, filed May 21, 2021; U.S. Provisional Patent Application No. 63/191,872, filed May 21, 2021; U.S. Provisional Patent Application No. 63/194,810, filed May 28, 2021; U.S. Provisional Patent Application No. 63/228,563, filed Aug. 2, 2021; U.S. Provisional Patent Application No. 63/228,572, filed Aug. 2, 2021; and U.S. Provisional Patent Application No. 63/228,594, filed Aug. 2, 2021, each of which is incorporated by reference in its entirety.

BACKGROUND

Improved formulations to administer hydrophobic active agents are desirable.

BRIEF DESCRIPTION

Various aspects of this disclosure relate to the discovery that hydrophobic active ingredients can be dissolved in propylene glycol and combined with a carbohydrate to produce a powder that is wetted by the propylene glycol, and that such powders are effective at dispersing hydrophobic active ingredients in beverages. Without limiting this disclosure or any patent claim that matures from this patent document, the propylene glycol and carbohydrate allow for the separation of hydrophobic active ingredients over a broad surface area, and the propylene glycol and carbohydrate can be dissolved in beverages rapidly enough to disperse the hydrophobic active ingredients in the beverage while minimizing the propensity of the hydrophobic active ingredients to recombine into a lipid phase.

DETAILED DESCRIPTION

Various aspects of this disclosure relate to a composition, comprising a solid phase and a liquid phase, wherein the solid phase has a surface-area-to-volume ratio that is greater than 500 per meter; the solid phase consists of ingredients; the ingredients of the solid phase comprise carbohydrates; the carbohydrates comprise one or more of alginic acid, alginate, propylene glycol alginate, inulin, arabinogalactan, lignosulfonate, carrageenan, furcelleran, pullulan, glucomannan, gellan gum, gum arabic, gellan gum, gum ghatti, guar gum, gum karaya, tara gum, tragacanth, xanthan gum, carboxymethylcellulose, hydroxyethyl cellulose, ethylhydroxyethylcellulose, hydroxypropyl cellulose, hydroxypropyl methylcellulose, modified starch, dextrin, polydextrose, pectin, beta-glucan, lactobionic acid, lactobionate, isomalt, erythritol, threitol, arabitol, xylitol, ribitol, mannitol, sorbitol, galactitol, fucitol, iditol, inositol, volemitol, sucrose, lactose, maltose, trehalose, maltitol, glucose, fructose, galactose, arabinose, ribose, xylose, allulose, sorbose, tagatose, fucose, mannose, and hydrogenated starch hydrolysate; at least 90 percent of the ingredients of the solid phase consist of the carbohydrates by mass; the composition comprises the liquid phase at a concentration of at least 0.5 percent and no greater than 15 percent by mass; the composition comprises the solid phase at a concentration of at least 85 percent and no greater than 99.5 percent by mass; the composition comprises at least 2 and no greater than 4 calories of food energy per gram of the composition; the liquid phase comprises a concentration of calories of food energy per gram of the liquid phase; the solid phase comprises a concentration of calories of food energy per gram of the solid phase that is less than the concentration of calories of food energy per gram of the liquid phase; the liquid phase consists of ingredients that comprise a solvent; each of the ingredients of the liquid phase has a concentration by mass in the liquid phase; the concentration by mass of the solvent in the liquid phase is greater than the concentration by mass of any of the other ingredients of the liquid phase; and the solvent is propane-1,2-diol.

"Comprise" refers to an open set such that ingredients that comprise a solvent can also comprise, for example, and active ingredient.

"Food calorie" refers to a North American food calorie, which is equal to a European Union food kilocalorie, and which are both equal to 4.184 kilojoules of food energy.

Various aspects of this disclosure relate to a container that contains at least 100 milligrams and no greater than 5 grams of a composition, wherein the composition comprises a solid phase and a liquid phase; the solid phase has a surface-area-to-volume ratio that is greater than 500 per meter; the solid phase consists of ingredients; the ingredients of the solid phase comprise carbohydrates; the carbohydrates comprise one or more sugar alcohols; at least 90 percent of the ingredients of the solid phase consist of the carbohydrates by mass; the composition comprises the liquid phase at a concentration of at least 0.5 percent and no greater than 15 percent by mass; the composition comprises the solid phase at a concentration of at least 85 percent and no greater than 99.5 percent by mass; the composition comprises at least 2 and no greater than 4 calories of food energy per gram of the composition; the liquid phase comprises a concentration of calories of food energy per gram of the liquid phase; the solid phase comprises a concentration of calories of food energy per gram of the solid phase that is less than the concentration of calories of food energy per gram of the liquid phase; the liquid phase consists of ingredients that comprise a solvent; each of the ingredients of the liquid phase has a concentration by mass in the liquid phase; the concentration by mass of the solvent in the liquid phase is greater than the concentration by mass of any of the other ingredients of the liquid phase; the solvent is propane-1,2-diol; the ingredients of the liquid phase comprise an active ingredient; the active ingredient is a solute that is dissolved in the solvent of the liquid phase; the active ingredient is dissolved in the solvent of the liquid phase at a concentration of at least 200 micromolar and no greater than 250 millimolar; the active ingredient has a solubility in water at 37 degrees Celsius; the active ingredient is dissolved in the solvent of the liquid phase at a concentration that is greater than the solubility of the active ingredient in water at 37 degrees Celsius; and the active ingredient has an octanol-water partition coefficient of at least 10.

Various aspects of this disclosure relate to a method to prepare a beverage formulation, comprising providing a composition comprising an active ingredient; providing a beverage; and combining the composition with the beverage to disperse the active ingredient in the beverage and to prepare the beverage formulation, wherein the composition comprises a solid phase and a liquid phase; the solid phase has a surface-area-to-volume ratio that is greater than 500 per meter; the solid phase consists of ingredients; the ingredients of the solid phase comprise carbohydrates; at least 90 percent of the ingredients of the solid phase consist of the carbohydrates by mass; the composition comprises the liquid phase at a concentration of at least 0.5 percent and no greater than 15 percent by mass; the composition comprises the solid phase at a concentration of at least 85 percent and no greater than 99.5 percent by mass; the composition comprises at least 0.5 and no greater than 5 calories of food energy per gram of the composition; the liquid phase comprises a concentration of calories of food energy per gram of the liquid phase; the solid phase comprises a concentration of calories of food energy per gram of the solid phase that is less than the concentration of calories of food energy per gram of the liquid phase; the liquid phase consists of ingredients that comprise a solvent; each of the ingredients of the liquid phase has a concentration by mass in the liquid phase; the concentration by mass of the solvent in the liquid phase is greater than the concentration by mass of any of the other ingredients of the liquid phase; the solvent is propane-1,2-diol; the ingredients of the liquid phase comprise the active ingredient; the active ingredient is a solute that is dissolved in the solvent of the liquid phase; the active ingredient is dissolved in the solvent of the liquid phase at a concentration of at least 200 micromolar and no greater than 250 millimolar; the active ingredient has a solubility in water at 37 degrees Celsius; the active ingredient is dissolved in the solvent of the liquid phase at a concentration that is greater than the solubility of the active ingredient in water at 37 degrees Celsius; the active ingredient has an octanol-water partition coefficient of at least 10; and the beverage is a liquid that comprises water at a concentration of at least 50 molar.

In some embodiments, the composition has a color; the beverage is colorless; and the beverage formulation has a color that is different from the color of the composition.

In some embodiments, the ingredients of the liquid phase comprise a curcumin derivative selected from 5-hydroxy-1, 7-bis(3-methoxy-4-oxocyclohexa-2,5-dienylidene)hepta-2, 4-diene-3-oxide; 5-hydroxy-1,7-bis(3-methoxy-4-oxocyclohexa-2,5-dienylidene)hepta-2,5-diene-3-oxide; 5-hydroxy-1,7-bis(3-methoxy-4-oxocyclohexa-2,5-dienylidene)hepta-3,5-diene-3-oxide; 5-oxo-1,7-bis(3-methoxy-4-oxocyclohexa-2,5-dienylidene)hept-2-ene-3-oxide; 5-oxo-1,7-bis(3-methoxy-4-oxocyclohexa-2,5-dienylidene)hept-3-ene-3-oxide; 2-methoxy-4-[3-hydroxy-5-oxo-7-(3-methoxy-4-oxocyclohexa-2,5-dienylidene)hepta-1,3-dienyl]phenolate; 2-methoxy-4-[5-hydroxy-3-oxo-7-(3-methoxy-4-oxocyclohexa-2,5-dienylidene)hepta-1,4-dienyl]phenolate; 2-methoxy-4-[5-hydroxy-3-oxo-7-(3-methoxy-4-oxocyclohexa-2,5-dienylidene)hepta-1,5-dienyl]phenolate; 2-methoxy-4-[3,5-dioxo-7-(3-methoxy-4-oxocyclohexa-2,5-dienylidene)hept-1-en-1-yl]phenolate; 2-methoxy-4-[3,5-dihydroxy-7-(3-methoxy-4-oxocyclohexa-2,5-dienylidene)hepta-1,3,5-trienyl]phenolate; 5-hydroxy-1-(4-hydroxy-3-methoxyphenyl)-7-(3-methoxy-4-oxocyclohexa-2,5-dienylidene)hepta-1,3,5-triene-3-oxide; 3-hydroxy-1-(4-hydroxy-3-methoxyphenyl)-7-(3-methoxy-4-oxocyclohexa-2,5-dienylidene)hepta-1,3,5-triene-5-oxide; 5-oxo-1-(4-hydroxy-3-methoxyphenyl)-7-(3-methoxy-4-oxocyclohexa-2,5-dienylidene)hepta-1,3-diene-3-oxide; 3-oxo-1-(4-hydroxy-3-methoxyphenyl)-7-(3-methoxy-4-oxocyclohexa-2,5-dienylidene)hepta-1,4-diene-5-oxide; 3-oxo-1-(4-hydroxy-3-methoxyphenyl)-7-(3-methoxy-4-oxocyclohexa-2,5-dienylidene)hepta-1,5-diene-5-oxide; 2-methoxy-4-[3-hydroxy-5-oxo-7-(4-hydroxy-3-methoxyphenyl)hepta-1,3,6-trienyl]phenolate; 2-methoxy-4-[5-hydroxy-3-oxo-7-(4-hydroxy-3-methoxyphenyl)hepta-1,4,6-trienyl]phenolate; and 2-methoxy-4-[3,5-dioxo-7-(4-hydroxy-3-methoxyphenyl)hepta-1,6-dienyl]phenolate.

In some embodiments, the method comprises recording video or images of the composition both prior to and subsequent to combining the composition with the beverage.

Various aspects of this disclosure relate to a method to market a composition, comprising disseminating over the internet the video or images recorded according to a method described anywhere in this patent document.

In some embodiments, the ingredients of the liquid phase comprise one or both of 1-hydroxypropane-2-oxide and 2-hydroxypropane-1-oxide. In some specific embodiments, the liquid phase comprises propane-1,2-diol and one or both of 1-hydroxypropane-2-oxide and 2-hydroxypropane-1-oxide at a molar ratio of at least 100:1 and no greater than 1,000,000:1 (propane-1,2-diol:1-hydroxypropane-2-oxide and 2-hydroxypropane-1-oxide).

In some embodiments, the method comprises comprising combining at least 100 milligrams and no greater than 5 grams of the composition with the beverage.

In some embodiments, the composition comprises at least 10 micrograms and no greater than 100 milligrams of the active ingredient.

In some embodiments, the method comprises administering the beverage formulation to a human, wherein the human self-administers the beverage formulation by drinking it.

In some embodiments, the human presents with a health condition, and the composition comprises an amount of the active ingredient that is effective to treat the health condition.

"Treat" refers to at least one of: to cure a health condition; to increase the probability that a health condition will be cured; to shorten the time over which a health condition is cured; to increase the probability that the time necessary to cure a health condition will be shortened; to decrease the severity of a health condition; to increase the probability that the severity of a health condition will decrease; to shorten the time over which the severity of a health condition is decreased; to increase the probability that the time necessary to decrease the severity of a health condition will be shortened; to inhibit a health condition from worsening; to increase the probability that a health condition will not worsen; to delay the worsening of a health condition; to increase the probability that the worsening of a health condition will be delayed; to inhibit the occurrence or recurrence of a health condition; to decrease the probability that a health condition will occur or reoccur; to delay the onset of a health condition; to increase the probability that the onset of a health condition will be delayed; to alleviate at least one symptom of a health condition; to increase the probability that at least one symptom of a health condition will be alleviated; to shorten the time over which at least one symptom of a health condition is alleviated; to increase the probability that the time necessary to alleviate at least one symptom of a health condition will be shortened; to decrease the severity of at least one symptom of a health condition; to increase the probability that the severity of at least one symptom of a health condition will be decreased; to shorten the time over which the severity of at least one symptom of a health condition is decreased; to increase the probability that the time necessary to decrease the severity of at least one symptom of a health condition will be shortened; to inhibit at least one symptom of a health condition from worsening; to increase the probability that at least one symptom of a health condition will not worsen; to delay the worsening of at least one symptom of a health condition; to increase the probability that the worsening of at least one symptom of a health condition will be delayed; to inhibit at least one symptom of a health condition from occurring or reoccurring; to decrease the probability that at least one symptom of a health condition will occur or reoccur; to delay the onset of at least one symptom of a health condition; and to increase the probability that the onset of at least one symptom of a health condition will be delayed.

In some embodiments, the health condition is epilepsy, anxiety, pain, or inflammation.

In some embodiments, the active ingredient is a cannabinoid.

In some embodiments, the active ingredient is a molecule selected from CBD, THC, Δ8-THC, CBG, CBDV, THCV, Δ8-THCV, CBGV, CBN, tetrahydrocannabiphorol, perrottetinene, nabilone, parahexyl, HUM-217, and HU-331; and the molecule has an acid dissociation constant in water for conversion of the molecule into the anion.

In some embodiments, the active ingredient is an anion; and a molecule selected from CBD, THC, Δ8-THC, CBG, CBDV, THCV, Δ8-THCV, CBGV, CBN, tetrahydrocannabiphorol, perrottetinene, nabilone, parahexyl, HUM-217, and HU-331 has an acid dissociation constant in water for conversion of the molecule into the anion.

In some embodiments, the molecule is CBD.

In some embodiments, the molecule is THC.

In some embodiments, the anion has the general structure I, II, or III; each skeletal atom is a carbon atom except that each asterisk (*) depicts an independent, optional substitution of a skeletal atom with either an oxygen atom, a sulfur atom, a sulfinyl, a sulfonyl, or a nitrogen atom; each cross (†) depicts an optional R group, which occurs for each odd-numbered R group that is bonded to a skeletal atom that is either a carbon atom or a nitrogen atom, which is omitted for each odd-numbered R group that is bonded to an oxygen atom, a sulfur atom, a sulfinyl, or a sulfonyl, which occurs for each even-numbered R group that is bonded to a skeletal atom that is a saturated carbon atom, and which is omitted for each even-numbered R group that is bonded to a skeletal atom that is an unsaturated carbon atom; exactly one R group is oxide, and this R group is selected such that the oxide is covalently bound to a carbon atom of an aromatic ring or an otherwise unsaturated carbon atom by a single bond; each dotted line depicts an optional double bond; an optional implicit hydrogen atom is bonded to each skeletal atom that is a carbon atom that is not bonded to an even-numbered R group; optional double bonds are selected and optional implicit hydrogen atoms are selected such that (i) the R group that is oxide is covalently bound to a carbon atom of an aromatic ring or an otherwise unsaturated carbon atom by a single bond, and (ii) no skeletal atom carries a full charge; and each R group is selected such that the anion comprises (i) at least 6 and no greater than 45 carbon atoms, (ii) at least 5 and no greater than 60 hydrogen atoms, (iii) at least 1 and no greater than 12 oxygen atoms, and (iv) no greater than 6 total combined sulfur, nitrogen, and halogen atoms.

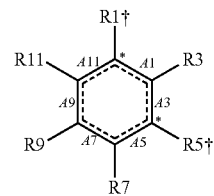

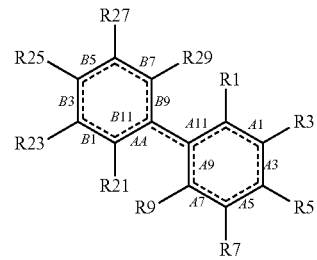

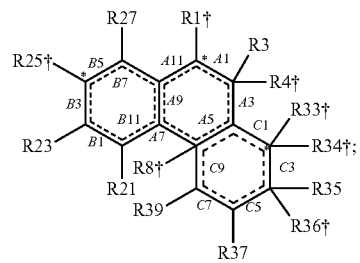

Odd-numbered R groups comprise R1, R3, R5, R7, R9, R11, R21, R23, R25, R27, R29, R35, R37, and R39. Even-numbered R groups comprise R4, R8, R34, and R36.

The following exemplification sets forth specific embodiments that do not limit the preceding disclosure or any claim that matures from this patent document.

EXEMPLIFICATION

The activity of formulations set forth in this disclosure is assayed in Sabra mice. 300 milligrams of a formulation is combined with 15 milliliters of water and administered by oral gavage. Each formulation comprises a liquid phase that contains propylene glycol and a solid phase that contains xylitol. The liquid phase contains a cannabinoid selected from CBD, THC, Δ8-THC, CBG, CBDV, THCV, Δ8-THCV, CBGV, CBC, CBN, tetrahydrocannabiphorol, perrottetinene, nabilone, parahexyl, HUM-217, and HU-331, which is dissolved in the propylene glycol, and controls lack any cannabinoid.

Zymosan is injected into the left hind paws of each mouse to induce pain, inflammation, and tumor necrosis factor ("TNF") signaling. Inflammatory paw swelling is measured with a caliper. Pain is measured with a Von Frey hair aesthesiometer. Plasma TNF is measured by HPLC. Formulations containing CBD, CBDV, HUM-217, and HU-331 each display robust reduction in pain, inflammation, and TNF signaling relative to controls. Formulations containing THC, Δ8-THC, CBG, THCV, Δ8-THCV, CBN, tetrahydrocannabiphorol, perrottetinene, nabilone, and parahexyl each display modest reduction in pain, inflammation, and TNF signaling relative to controls. The formulation containing CBC displays no detectable effect on pain, inflammation, and TNF signaling relative to controls.

The invention claimed is:

1. A method to prepare a beverage formulation, comprising:
providing a composition comprising an active ingredient;
providing a beverage; and
combining the composition with the beverage to disperse the active ingredient in the beverage and to prepare the beverage formulation,
wherein:
the composition comprises a solid phase and a liquid phase;
the solid phase has a surface-area-to-volume ratio that is greater than 500 per meter;
the solid phase consists of ingredients;
the ingredients of the solid phase comprise carbohydrates;
at least 90 percent of the ingredients of the solid phase consist of the carbohydrates by mass;
the composition comprises the liquid phase at a concentration of at least 0.5 percent and no greater than 15 percent by mass;
the composition comprises the solid phase at a concentration of at least 85 percent and no greater than 99.5 percent by mass;
the composition comprises at least 0.5 and no greater than 5 calories of food energy per gram of the composition;
the liquid phase comprises a concentration of calories of food energy per gram of the liquid phase;
the solid phase comprises a concentration of calories of food energy per gram of the solid phase that is less than the concentration of calories of food energy per gram of the liquid phase;
the liquid phase consists of ingredients that comprise a solvent;
each of the ingredients of the liquid phase has a concentration by mass in the liquid phase;
the concentration by mass of the solvent in the liquid phase is greater than the concentration by mass of any of the other ingredients of the liquid phase;
the solvent is propane-1,2-diol;
the ingredients of the liquid phase comprise the active ingredient;
the active ingredient is a solute that is dissolved in the solvent of the liquid phase;
the active ingredient is dissolved in the solvent of the liquid phase at a concentration of at least 200 micromolar and no greater than 250 millimolar;
the active ingredient has a solubility in water at 37 degrees Celsius;
the active ingredient is dissolved in the solvent of the liquid phase at a concentration that is greater than the solubility of the active ingredient in water at 37 degrees Celsius;
the active ingredient has an octanol-water partition coefficient of at least 10; and
the beverage is a liquid that comprises water at a concentration of at least 50 molar.

2. The method of claim 1, comprising recording video or images of the composition both prior to and subsequent to combining the composition with the beverage.

3. The method of claim 1, comprising combining at least 100 milligrams and no greater than 5 grams of the composition with the beverage.

4. The method of claim 1, wherein the composition comprises at least 10 micrograms and no greater than 100 milligrams of the active ingredient.

5. The method of claim 1, wherein the active ingredient is cannabidiol (CBD).

6. The method of claim 1, wherein the active ingredient is tetrahydrocannabinol (THC).

7. The method of claim 1, wherein the active ingredient is delta8-tetrahydrocannabinol ($\Delta$8-THC).

8. The method of claim 1, wherein the active ingredient is cannabigerol (CBG).

9. The method of claim 1, wherein the active ingredient is cannabidivarin (CBDV).

10. The method of claim 1, wherein the active ingredient is tetrahydrocannabivarin (THCV).

11. The method of claim 1, wherein the active ingredient is delta8-tetrahydrocannabivarin ($\Delta$8-THC).

12. The method of claim 1, wherein the active ingredient is cannabigerovarin (CBGV).

13. The method of claim 1, wherein the active ingredient is cannabinol (CBN).

14. The method of claim 1, wherein the active ingredient is tetrahydrocannabiphorol.

15. The method of claim 1, wherein the active ingredient is perrottetinene.

16. The method of claim 1, wherein the active ingredient is nabilone.

17. The method of claim 1, wherein the active ingredient is parahexyl.

18. The method of claim 1, wherein the active ingredient is HU-331.

* * * * *